US007682817B2

(12) United States Patent
Cohen et al.

(10) Patent No.: US 7,682,817 B2
(45) Date of Patent: Mar. 23, 2010

(54) MICROFLUIDIC ASSAY DEVICES

(75) Inventors: David Samuel Cohen, Alpharetta, GA (US); Shawn Ray Feaster, Duluth, GA (US)

(73) Assignee: Kimberly-Clark Worldwide, Inc.

( * ) Notice: Subject to any disclaimer, the term of this patent is extended or adjusted under 35 U.S.C. 154(b) by 1141 days.

(21) Appl. No.: 11/021,545

(22) Filed: Dec. 23, 2004

(65) Prior Publication Data

US 2006/0137434 A1 Jun. 29, 2006

(51) Int. Cl.
*C12M 1/36* (2006.01)

(52) U.S. Cl. .............. 435/287.1; 435/286.5; 435/288.2; 435/288.5; 422/129; 422/140; 422/156; 436/524

(58) Field of Classification Search ....................... None
See application file for complete search history.

(56) References Cited

U.S. PATENT DOCUMENTS

| | | | |
|---|---|---|---|
| 4,094,647 | A | 6/1978 | Deutsch et al. |
| 4,168,146 | A | 9/1979 | Grubb et al. |
| RE30,267 | E | 5/1980 | Bruschi |
| 4,363,874 | A | 12/1982 | Greenquist |
| 4,366,241 | A | 12/1982 | Tom et al. |
| 4,480,042 | A | 10/1984 | Craig et al. |
| 4,756,884 | A | 7/1988 | Hillman et al. |
| 4,806,312 | A | 2/1989 | Greenquist |
| 4,855,240 | A | 8/1989 | Rosenstein et al. |
| 4,857,453 | A | 8/1989 | Ullman et al. |
| 4,963,498 | A | 10/1990 | Hillman et al. |
| 5,145,784 | A | 9/1992 | Cox et al. |
| 5,234,813 | A | 8/1993 | McGeehan et al. |
| 5,352,582 | A | 10/1994 | Lichtenwalter et al. |
| 5,395,754 | A | 3/1995 | Lambotte et al. |

(Continued)

FOREIGN PATENT DOCUMENTS

| | | |
|---|---|---|
| EP | 26924 | 6/1988 |

(Continued)

OTHER PUBLICATIONS

Article —*Flow-Based Microimunoassay*, Mark A. Hayes, Nolan A. Polson, Allison N. Phayre, and Antonio A. Garcia, Analytical Chemistry, vol. 73, No. 24, Dec. 15, 2001, pp. 5896-5902.

(Continued)

*Primary Examiner*—N. Yang
(74) *Attorney, Agent, or Firm*—Dority & Manning, P.A.

(57) ABSTRACT

A microfluidic assay device for determining the presence or absence of an analyte within a fluid test sample is provided. The present invention provides a technique for achieving continuous flow in a microfluidic device by using at least one input channel, an analysis zone, and a plurality of wicking channels disposed about the perimeter of the analysis zone. In one embodiment, for example, the wicking channels extend radially from the analysis zone. As a result of the particular configuration of the microfluidic device, an assay may performed in a "single step" without the need for active forces, such as a pressure source, electrokinetic force, etc., to induce flow of the fluid test sample through the device. Likewise, flow rate is controlled so that the dwell time of the fluid test sample within the analysis zone is long enough to allow for the desired reactions and/or detection.

25 Claims, 8 Drawing Sheets

U.S. PATENT DOCUMENTS

| | | | |
|---|---|---|---|
| 5,424,220 A | 6/1995 | Goerlach-Graw et al. | |
| 5,478,527 A | 12/1995 | Gustafson et al. | |
| 5,489,988 A | 2/1996 | Ackley et al. | |
| 5,500,350 A | 3/1996 | Baker et al. | |
| 5,624,537 A | 4/1997 | Turner et al. | |
| 5,736,188 A | 4/1998 | Alcock et al. | |
| 5,965,237 A | 10/1999 | Bruin et al. | |
| 6,027,944 A | 2/2000 | Robinson et al. | |
| 6,057,165 A | 5/2000 | Mansour | |
| 6,099,484 A | 8/2000 | Douglas et al. | |
| 6,103,537 A | 8/2000 | Ullman et al. | |
| 6,156,270 A | 12/2000 | Buechler et al. | |
| 6,183,972 B1 | 2/2001 | Kuo et al. | |
| 6,221,579 B1 | 4/2001 | Everhart et al. | |
| 6,271,040 B1 | 8/2001 | Buechler | |
| 6,274,384 B1 | 8/2001 | Starzl et al. | |
| 6,303,288 B1 | 10/2001 | Furcht et al. | |
| 6,399,295 B1 | 6/2002 | Kaylor et al. | |
| 6,399,398 B1 | 6/2002 | Cunningham et al. | |
| 6,416,642 B1 | 7/2002 | Alajoki et al. | |
| 6,436,722 B1 | 8/2002 | Clark et al. | |
| 6,481,453 B1 | 11/2002 | O'Connor et al. | |
| 6,498,497 B1 | 12/2002 | Chow et al. | |
| 6,509,085 B1 | 1/2003 | Kennedy | |
| 6,518,168 B1 | 2/2003 | Clem et al. | |
| 6,573,040 B2 | 6/2003 | Everhart et al. | |
| 6,579,673 B2 | 6/2003 | McGrath et al. | |
| 6,585,939 B1 | 7/2003 | Dapprich | |
| 6,653,089 B2 | 11/2003 | Takayama et al. | |
| 6,887,332 B1 | 5/2005 | Kagan et al. | |
| 6,982,165 B2 * | 1/2006 | Yamakawa et al. | 435/287.2 |
| 2001/0055812 A1 * | 12/2001 | Mian et al. | 436/45 |
| 2002/0005354 A1 * | 1/2002 | Spence et al. | 204/450 |
| 2002/0012616 A1 * | 1/2002 | Zhou et al. | 422/130 |
| 2003/0017615 A1 | 1/2003 | Sidwell et al. | |
| 2003/0118480 A1 | 6/2003 | Kaylor et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2004/0035792 A1 | 2/2004 | Rauch et al. | |
| 2004/0043507 A1 | 3/2004 | Song et al. | |
| 2004/0043511 A1 | 3/2004 | Song et al. | |
| 2004/0106190 A1 | 6/2004 | Yang et al. | |
| 2004/0115861 A1 | 6/2004 | Wong et al. | |
| 2004/0163758 A1 | 8/2004 | Kagan et al. | |
| 2006/0057245 A1 | 3/2006 | Haupt et al. | |

FOREIGN PATENT DOCUMENTS

| | | |
|---|---|---|
| WO | WO 9734148 | 9/1997 |
| WO | WO 0050891 A1 | 8/2000 |
| WO | WO 0078917 A1 | 12/2000 |
| WO | WO 0198785 A2 | 12/2001 |
| WO | WO 0198785 A3 | 12/2001 |
| WO | WO 03008971 A2 | 1/2003 |
| WO | WO 03008971 A3 | 1/2003 |

OTHER PUBLICATIONS

International Search Report.

* cited by examiner

MICROFLUIDIC ASSAY DEVICES

BACKGROUND OF THE INVENTION

Microfluidic devices have been used in biochemical fields to perform high throughput screening assays. Microfluidic devices provide fluidic networks in which biochemical reactions, sample injections, and separation of reaction products may be achieved. In many conventional microfluidic devices, fluid flow and reagent mixing are achieved using electrokinetic transport phenomena (electroosmotic and electrophoretic). Electrokinetic transport is controlled by regulating the applied potentials at the terminus of each channel of the microfluidic device. Within the channel network, cross intersections and mixing tees are used for valving and dispensing fluids with high volumetric reproducibility. The mixing tee may be used to mix proportionately two fluid streams in ratio from 0 to 100% from either stream simply by varying the relative field strengths in the two channels.

Unfortunately, the use of active (or external) forces to induce flow is cost prohibitive and overly complex. Thus, other microfluidic devices have also been developed. For example, U.S. Pat. No. 6,416,642 to Alajoki, et al. describes a device that utilizes a wick (which may be pre-wetted, dry or wetted in position in contact with a microfluidic system) that acts by capillary action to draw material through channels or wells in which it is placed in fluidic contact. Alternatively, or additionally, a volume of liquid is optionally injected or withdrawn downstream of the material or region of interest, and the flow rate modulated by creating a pressure differential at the site of injection. However, problems still exist with such conventional microfluidic devices. For example, the flow rate through the device may sometimes be too fast to handle the data acquisition or necessary reaction time.

As such, a need still exists for an improved microfluidic assay device that is relatively inexpensive, easy to use, and that is capable of effectively and accurately determine the presence or concentration of an analyte within a fluid test sample.

SUMMARY OF THE INVENTION

In accordance with one embodiment of the present invention, an assay device is disclosed for detecting the presence or concentration of an analyte within a fluid test sample. The assay device comprises an input channel and an analysis zone in fluid communication therewith. The analysis zone serves as a location for detecting the analyte. The assay device also comprises a plurality of wicking channels extending outwardly from a periphery of the analysis zone, wherein the assay device is configured so that the fluid test sample is capable of flowing through the input channel and the analysis zone primarily via capillary action.

In accordance with another embodiment of the present invention, a method is disclosed for performing an assay. The method comprises introducing into an input channel a fluid test sample suspected of containing an analyte. The fluid is allowed to flow via capillary action from the input channel to an analysis zone that defines a periphery. The presence or absence of the analyte is detected. The fluid test sample is drawn from the analysis zone using a plurality of wicking channels that extend outwardly from the periphery of the analysis zone.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
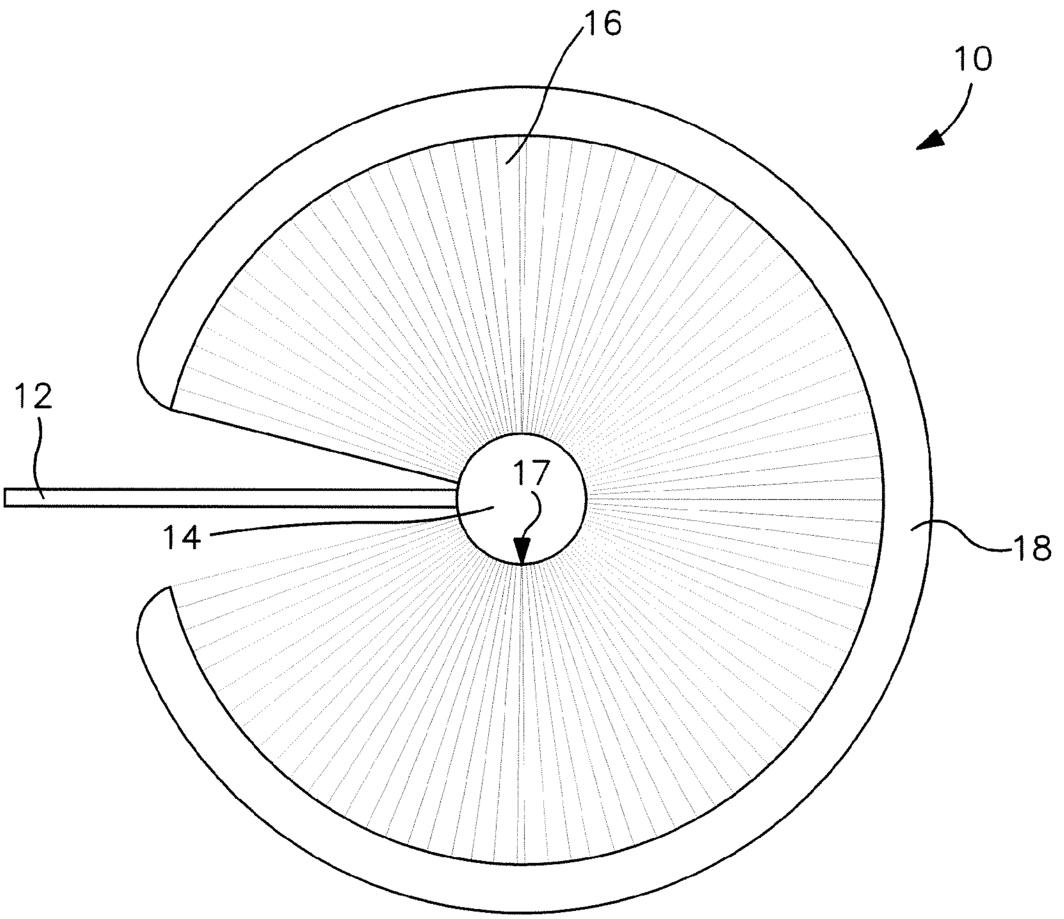
FIG. 1 is a schematic illustration of one embodiment of a microfluidic assay device of the present invention.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin; creatinine kinase MB (CK-MB); digoxin; phenytoin; phenobarbitol; carbamazepine; vancomycin; gentamycin; theophylline; valproic acid; quinidine; luteinizing hormone (LH); follicle stimulating hormone (FSH); estradiol, progesterone; C-reactive protein; lipocalins; IgE antibodies; cytokines; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); influenza virus; thyroid stimulating hormone (TSH); thyroxine (T4); total triiodothyronine (Total T3); free triiodothyronine (Free T3); carcinoembryoic antigen (CEA); lipoproteins, cholesterol, and triglycerides; and alpha fetoprotein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 6,436,651 to Everhart, et al. and U.S. Pat. No. 4,366,241 to Tom et al.

As used herein, the term "fluid test sample" generally refers to a fluid suspected of containing the analyte. The fluid test sample may, for instance, include materials obtained directly from a source, as well as materials pretreated using techniques, such as, but not limited to, filtration, precipitation, dilution, distillation, mixing, concentration, inactivation of interfering components, the addition of reagents, and so forth. The fluid test sample may be derived from a biological source, such as a physiological fluid, including, blood, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen, and so forth. Besides physiological fluids, other liquid samples may be used, such as water, food products, and so forth.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

In general, the present invention is directed to a microfluidic device for determining the presence or absence of an analyte within a fluid test sample. The present invention provides a technique for achieving continuous flow in a microfluidic device by using at least one input channel, an analysis zone, and a plurality of wicking channels disposed about the perimeter of the analysis zone. In one embodiment, for example, the wicking channels extend radially from the analysis zone. As a result of the particular configuration of the microfluidic device, an assay may performed in a "single step" without the need for active forces, such as a pressure source, electrokinetic force, etc., to induce flow of the fluid test sample through the device. Likewise, flow rate is controlled so that the dwell time of the fluid test sample within the analysis zone is long enough to allow for the desired reactions and/or detection.

A. Microfluidic Assay Device

The microfluidic device of the present invention contains one or more zones through which a fluid is capable of flowing. As used herein, the term "microfluidic device" includes any device that employs one or more fluidic zones having a "capillary scale" dimension, such as a cross-sectional area of less than about 20 square millimeters. However, as will be discussed in more detail below, the microfluidic device may also possess one or more fluidic zones having larger than capillary-scale dimensions for a variety of purposes, such as increasing surface area reaction volume, accommodating highly dilute samples, providing an area for detection, and so forth.

The type and number of fluidic zones selected will depend on the analyte of interest, the detection method utilized, and other factors relating to the nature of the device and the fluid test sample. Referring to FIG. 1, for example, one embodiment of a microfluidic device 10 will now be described in more detail. As shown, the microfluidic device 10 includes at least one input channel 12 that may serve as a location for a user to apply the fluid test sample. Alternatively, the input channel 12 may be in communication with a sample well (e.g., chamber, reservoir, port, etc.), to which the fluid test sample is initially added before flowing to the input channel 12. The well may be open or closed within the body of the device 10. In addition, as is well known in the art, a network of channels 12 interconnected by a T-junction, Y-junction, etc., may also be utilized. Examples of such microfluidic channel networks are described in more detail in U.S. Pat. No. 6,481,453 to O'Connor, et al. and U.S. Pat. No. 6,416,642 to Alajoki, et al., which are incorporated herein in their entirety by reference thereto for all purposes. The channel 12 may have any desired cross-sectional shape, such as circular, square, rectangular, triangular, trapezoidal, v-shaped, u-shaped, hexagonal, octagonal, irregular, and so forth. Further, the channel 12 may be straight, tapered, curved, serpentine, labyrinth-like, or have any other desired configuration.

Regardless of the shape selected, the dimensions of the channel 12 are generally such that passive capillary flow drives the flow of the fluid test sample through the channel 12 to other zones of the device 10. Capillary flow generally occurs when the adhesive forces of a fluid to the walls of a channel are greater than the cohesive forces between the liquid molecules. Specifically, capillary pressure is inversely proportional to the cross-sectional dimension of the channel and directly proportional to the surface tension of the liquid, multiplied by the cosine of the contact angle of the fluid in contact with the material forming the channel. Thus, to facilitate capillary flow in the device 10, the cross-sectional dimension (e.g., width, diameter, etc.) of the channel 12 may be selectively controlled, with smaller dimensions generally resulting in higher capillary pressure. For example, in some embodiments, the cross-sectional dimension of the channel 12 is less than about 10 millimeters, in some embodiments from about 0.001 to about 5 millimeters, and in some embodiments, from about 0.01 to about 2 millimeters. Of course, the cross-sectional dimension of the channel 12 may also vary as a function of length. The height or depth of the channel 12 may also vary to accommodate different volumes of the fluid test sample. For example, the depth of the channel 12 may be from about 0.1 micrometers to about 1,000 micrometers, in some embodiments from about 5 micrometers to about 500 micrometers, and in some embodiments, from about 20 micrometers to about 100 micrometers.

The cross-sectional area of the channel 12 may also vary. For example, the cross-sectional area is typically less than about 20 square millimeters, in some embodiments from about 0.001 to about 10 square millimeters, and in some embodiments, from about 0.01 to about 5 square millimeters. Further, the aspect ratio (cross-sectional dimension/depth) of the channel 12 may range from about 0.1 to about 200, in some embodiments from about 0.2 to about 100, and in some embodiments from about 0.5 to about 50. In cases where the cross-sectional dimension (e.g., width, diameter, etc.) and/or height vary as a function of length, the aspect ratio is determined from the average dimensions. Likewise, the length of the channel 12 may vary. For example, the channel 12 may have a length that is from about 1 millimeter to about 50 centimeters, and in some embodiments, from about 5 millimeters to about 50 millimeters. Channels having greater lengths may be particularly desired in cases where reagents are mixed with the fluid test sample to allow an adequate amount of time for mixing.

The channel 12 is in fluid communication with an analysis zone 14 where detection of an analyte may occur. As shown in FIG. 1, for example, the fluid test sample may flow sequentially from the channel 12 to the analysis zone 14. In other embodiments, however, the fluid test sample may also flow through other fluidic zones (e.g., washing zones, mixing zones, etc.) before reaching the analysis zone 14. Generally speaking, the analysis zone 14 is configured to accommodate the entire volume of the fluid test sample, as well as any reagents in the performance of the assay. This ensures that at least a significant portion of the analyte within the fluid test sample contacts any desired reagents contained within the analysis zone 14, thereby improving the accuracy of the obtained results. It is also desirable that the size and shape of the analysis zone 14 be selected so that the flow rate of the fluid test sample is slow enough to allow for detection of the analyte. Thus, in some embodiments, the cross-sectional dimension (e.g., width, diameter, etc.) of the analysis zone 14 may range from about 0.5 micrometers to about 20 millimeters, in some embodiments from about 5 micrometers to about 10 millimeters, and in some embodiments, from about 20 micrometers to about 5 millimeters. Likewise, the depth of the analysis zone 14 may range from about 0.1 micrometers to about 5 millimeters, in some embodiments from about 5 micrometers to about 3 millimeters, and in some embodiments, from about 20 micrometers to about 1 millimeter. In addition, some suitable cross-sectional shapes for the analysis zone 14 include, but are not limited to, circular, square, rectangular, triangular, trapezoidal, v-shaped, u-shaped, hexagonal, octagonal, irregular, and so forth. In the embodiment illustrated in FIG. 1, for example, the analysis zone 14 has a circular shape (e.g., ring) in which the cross-sectional dimension of the zone 14 is defined as the difference in the outer diameter and the inner diameter of the ring.

One beneficial aspect of the microfluidic device 10 is that it does not require active forces (e.g., pressure source, electrokinetic force, etc.) to induce fluid flow of the fluid test sample through the device 10. As discussed above, this is partly due to the particular geometry selected for the channel 12 and analysis zone 14. In addition, however, the microfluidic device 10 also contains a plurality of microfluidic, wicking channels 16 that are in fluid communication with the analysis zone 14. The wicking channels 16 help control the flow rate of the fluid by modulating its pressure downstream from the channel 12 and analysis zone 14. For example, an interface may form between the fluid and air at the opening of the channel 12, between the channel 12 and the analysis zone 14, and so forth. Once formed, the air/fluid interface reduces the ability of the fluid to flow via capillary pressure through the device 10, thereby inhibiting full development of the assay. The wicking channels 16 help force the air/fluid interface through the device 10. Also, when drawn toward the wicking channels 16, the air/fluid interface may actually serve as a washing agent, removing unbound reagents and other materials from the system as the assay develops.

Still another benefit of the wicking channels 16 is that they help slow down the flow rate of the fluid while present in the analysis zone 14. Specifically, at the interface of the analysis zone 14 and wicking channels 16, the analysis zone 14 typically has a cross-sectional area that is greater than the wicking channels 16. Thus, fluid passing from the analysis zone 14 to the wicking channels 16 will experience a drop in pressure that results in a reduction in flow rate. The difference in fluid flow rate between the analysis zone 14 and the wicking channels 16 also results in some backpressure, which although not large enough to overcome the capillary pressure of the fluid, does slow down the fluid flow in the analysis zone 14. For example, after application to the device 10, most, if not all, of the fluid test sample may exit the analysis zone 14 after a total dwell time of from about 1 to about 20 minutes, in some embodiments 2 to about 18 minutes, and in some embodiments, from about 3 to about 15 minutes. Of course, the total dwell time may widely vary based on a variety of factors, such as the volume of the fluid test sample the analysis zone 14 is required to accommodate, the number and size of the employed fluidic zones, the nature of the fluid test sample, etc. For example, the rheological properties of the fluid may affect its total dwell time. That is, less viscous fluids (e.g., urine, water, etc.) tend to be flow at a faster rate than more viscous fluids (e.g., blood). If desired, the design parameters of the device 10 may also be selectively tailored for either low or high viscosity fluids.

To achieve the desired control over fluid flow rate, the size, shape, and placement of the wicking channels 16 are selectively controlled. Generally speaking, the wicking channels 16 may have any desired cross-sectional shape, such as circular, square, rectangular, triangular, trapezoidal, v-shaped, u-shaped, hexagonal, octagonal, irregular, and so forth. Also, the shape of the wicking channels 16 may vary as a function of length, such as tapering inwardly or outwardly in the direction of the analysis zone 14. In such cases, the narrower portion of the wicking channels 16 may be positioned adjacent to and/or within the analysis zone 14. This results in a higher pressure drop at an interface 17 of the wicking channels 16 and analysis zone 14, in turn resulting in a lower flow rate of the fluid through the analysis zone 14.

To enhance the ability of the wicking channels 16 to draw fluid from the analysis zone 14 and to slow the flow rate of the fluid therethrough, the cross-sectional dimension of the wicking channels 16 may also be selectively controlled. Narrower wicking channels, for example, may provide a slower flow rate than wider wicking channels. In some embodiments, the cross-sectional dimension of the wicking channels 16 is typically less than about 500 micrometers, in some embodiments from about 5 micrometers to about 300 micrometers, and in some embodiments, from about 10 micrometers to about 200 micrometers. As indicated above, the cross-sectional dimension of the wicking channels 16 may vary as a function of its length, such as tapering inwardly in the direction of the analysis zone 14. In such cases, the maximum cross-sectional dimension of the wicking channels 16 may optionally fall within the exemplary ranges set forth above. The height or depth of the wicking channels 16 may also vary to accommodate different volumes of the fluid test sample. For example, the depth of the wicking channels 16 may be from about 0.5 micrometers to about 500 micrometers, in some embodiments from about 5 micrometers to about 300 micrometers, and in some embodiments, from about 10 micrometers to about 100 micrometers.

The cross-sectional area of the wicking channels 16 may also vary. For example, the cross-sectional area is typically less than about 20 square millimeters, in some embodiments from about 0.001 to about 10 square millimeters, and in some embodiments, from about 0.01 to about 5 square millimeters. Moreover, the aspect ratio (cross-sectional dimension/depth) of the wicking channels 16 may range from about 0.1 to about 10, in some embodiments from about 0.25 to about 5, and in some embodiments from about 0.5 to about 1.5. In cases where the cross-sectional dimension (e.g., width, diameter, etc.) and/or height vary as a function of length, the aspect ratio is determined from the average dimensions. Likewise, the length of the wicking channels 16 may also range from about 1 millimeter to about 50 centimeters, and in some embodiments, from about 5 millimeters to about 50 millimeters.

Apart from the selected materials and geometry, the physical arrangement of the wicking channels 16 also helps achieve the desired control over flow rate. For example, to facilitate a more uniform and controlled flow rate within the analysis zone 14, it is generally desired that the wicking channels 16 extend outwardly from the periphery of the analysis zone 14. In this manner, the wicking channels 16 may effectively draw fluid from the analysis zone 14 at a rate that is slow enough to provide the desired dwell time. In the embodiment illustrated in FIG. 1, for instance, the wicking channels 16 extend radially from the periphery of the circular-shaped analysis zone 14. The spacing between the wicking channels 16 may also vary depending on the desired affect on the flow rate of the fluid test sample. For example, the wicking channels 16 may be positioned directly adjacent to each other or spaced at a small distance from each other, such as from about 0.1 to about 500 micrometers, in some embodiments from 0.5 to about 100 micrometers, and in some embodiments, from about 1 to about 50 micrometers. Although not required, it is typically desired that the wicking channels 16 be spaced equidistant from each other so that a uniform flow rate is achieved. The number of wicking channels 16 may also vary depending on their size, spacing, and the size and shape of the analysis zone 14. For example, a large number of wicking channels may draw fluid from the analysis zone 14 at a faster rate than a small number of wicking channels. In some embodiments, the number of wicking channels 16 may vary from about 3 to about 500, in some embodiments from about 15 to about 200, and in some embodiments, from about 20 to about 80.

Although not required, certain embodiments of the present invention may employ an absorbent material in one or more of the wicking channels 16 to improve flow rate control. Some suitable absorbent materials that may be used to form the wicking channels include, but are not limited to, nitrocellulose, cellulosic materials, porous polyethylene pads, glass fiber filter paper, and so forth. The absorbent material may be wet or dry prior to being incorporated into the microfluidic assay device. Pre-wetting may facilitate capillary flow for some fluids, but is not typically required. Also, as is well known in the art, the wicking channels 16 may include a surfactant to assist the wicking process.

Besides the above-mentioned fluidic zones, other optional zones may also be utilized in the microfluidic device 10. For example, as shown in FIG. 1, an overflow zone 18 may be placed in fluid communication with the wicking channels 16 for receiving a fluid after it traverses therethrough. The shape and/or size of the overflow zone 18 may vary widely depending on the desired volume of liquid. For example, in the embodiment illustrated in FIG. 1, the overflow zone 18 has a substantially circular shape. Moreover, the cross-sectional dimension of the overflow zone 18 may range from about 0.1 to about 10 millimeters, in some embodiments from about 0.5 to about 8 millimeters, and in some embodiments, from about 1 to about 4 millimeters. A narrower overflow zone 18, for example, may provide a slower flow rate. If desired, the cross-sectional dimension of the overflow zone 18 may vary as a function of its length, such as tapering outwardly from the direction of the analysis zone 14. The height or depth of the overflow zone 18 may also vary to accommodate different volumes of the fluid test sample. For example, the depth of the overflow zone 18 may be from about 0.1 micrometers to about 5 millimeters, in some embodiments from about 5 micrometers to about 3 millimeters, and in some embodiments, from about 20 micrometers to about 1 millimeter. If desired, the overflow zone 18 may also contain an aperture to allow for the displacement of air that traverses through the device 10.

Further, the microfluidic device 10 may also include other zones that serve a variety of purposes. For example, the microfluidic device 10 may include a washing zone (not shown) that provides for the flow of a washing reagent to the analysis zone to remove any unbound reagents. Examples of washing agents may include, for instance, water, a buffer solution, such as PBS buffer, HEPES buffer, etc., and so forth. In addition, a reagent zone (not shown) may also be provided through which affinity reagents (e.g., capture ligands, redox mediators, particles, labels, etc.) may flow to initiate a desired reaction. If desired, the additional washing and reagent zones may be formed in the manner described above. By using separate and distinct sample addition, washing, and reagent zones, controlled and sequential delivery of different solutions may be provided.

Figure 2:
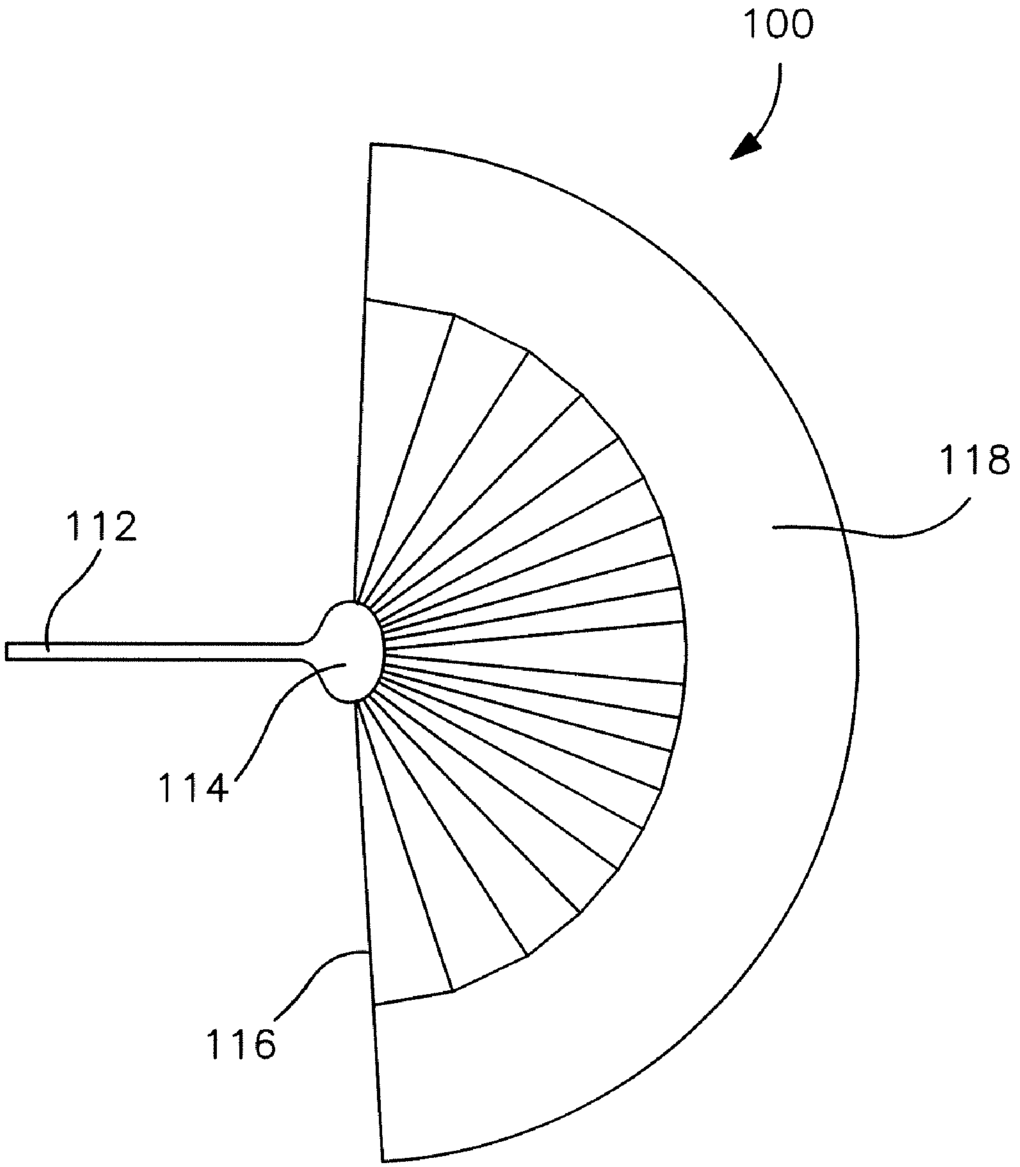
FIGS. 2-7 are schematic illustrations of other embodiments of the microfluidic assay device of the present invention.
Figure 3:
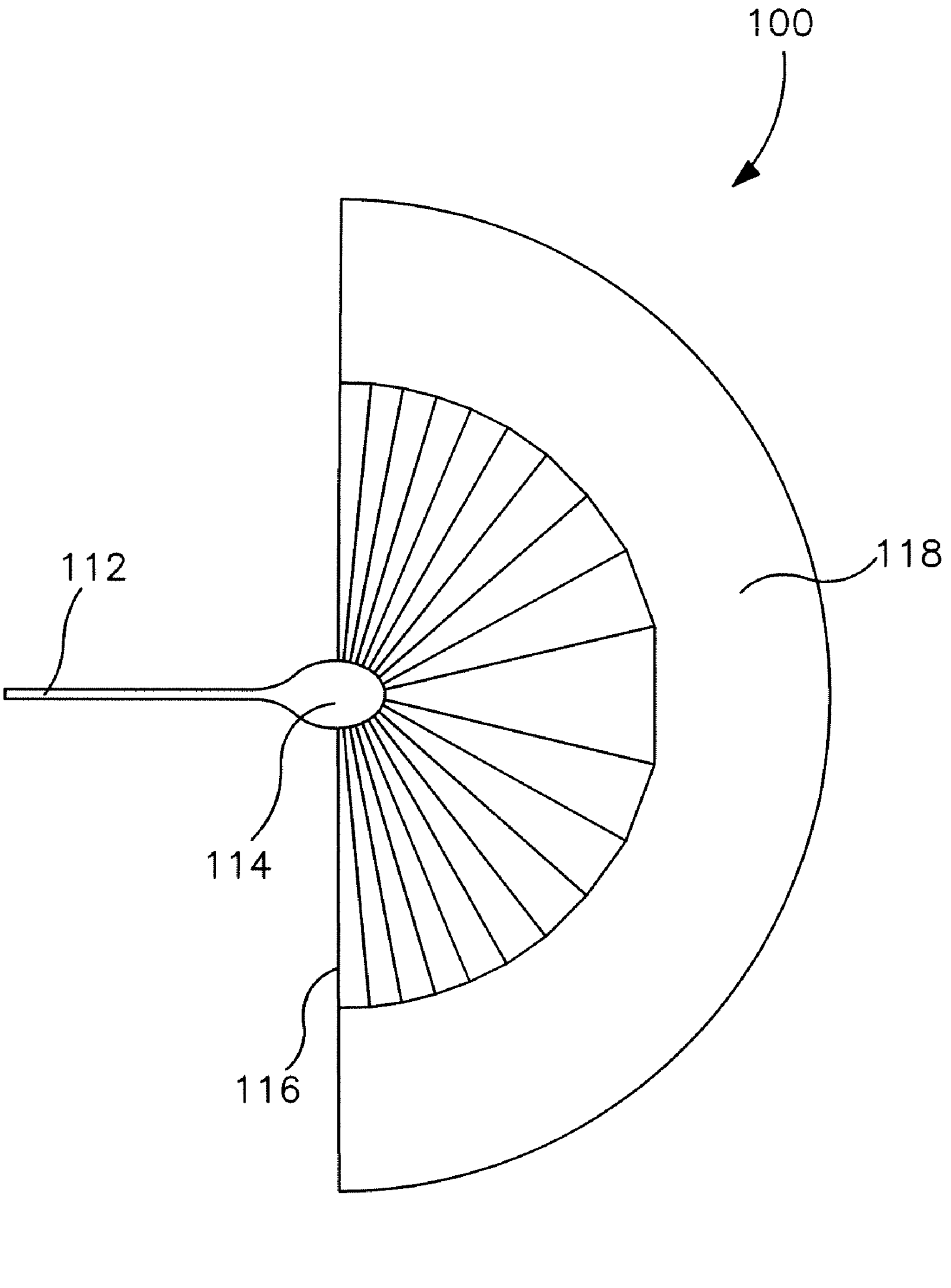
Figure 4:
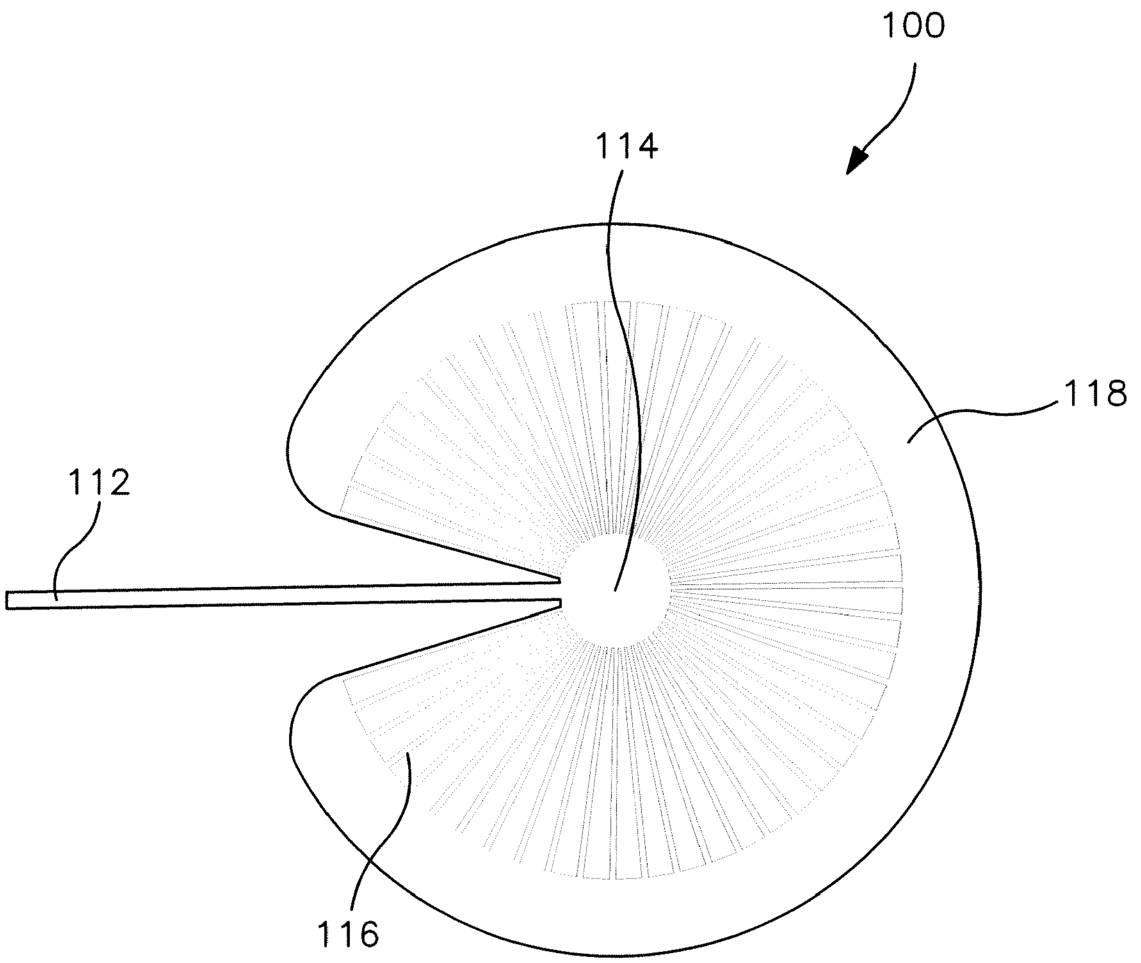
Figure 5:
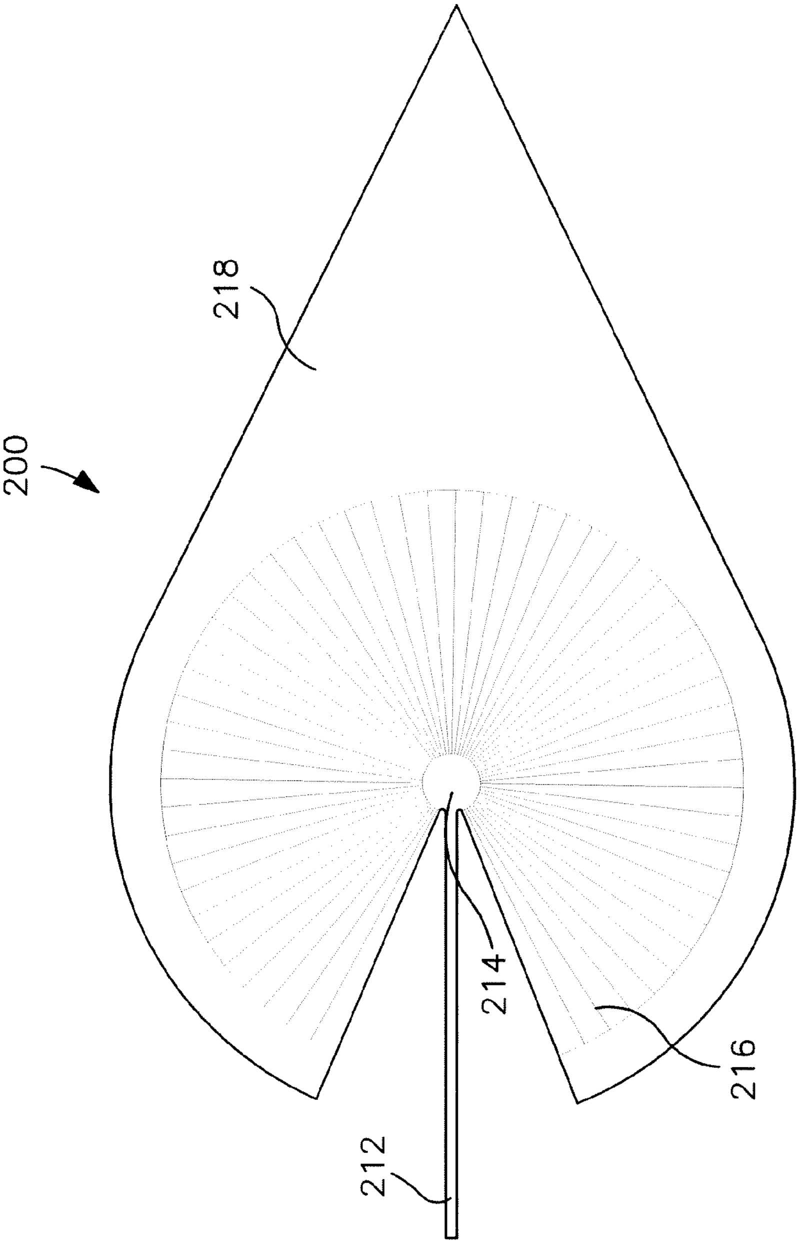
Figure 6:
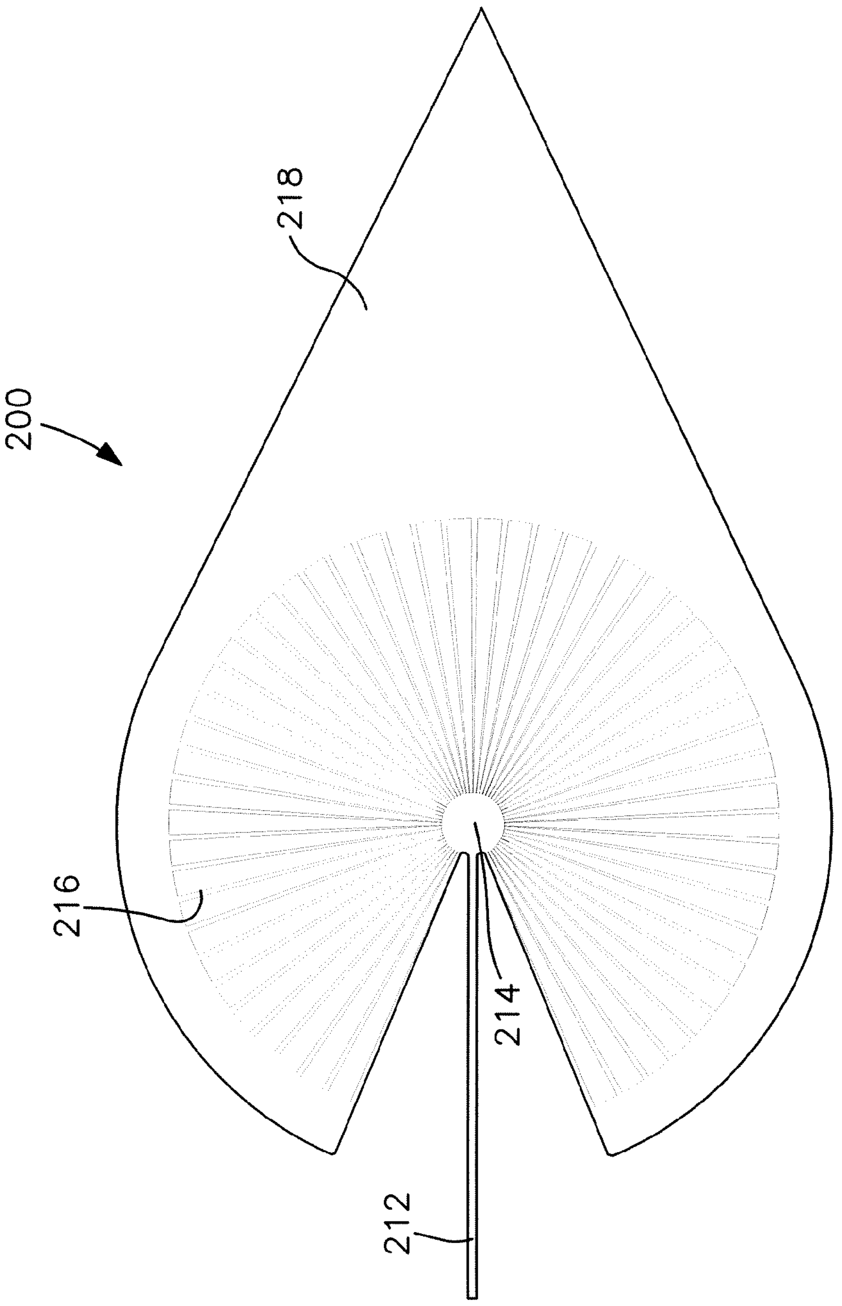
Figure 7:
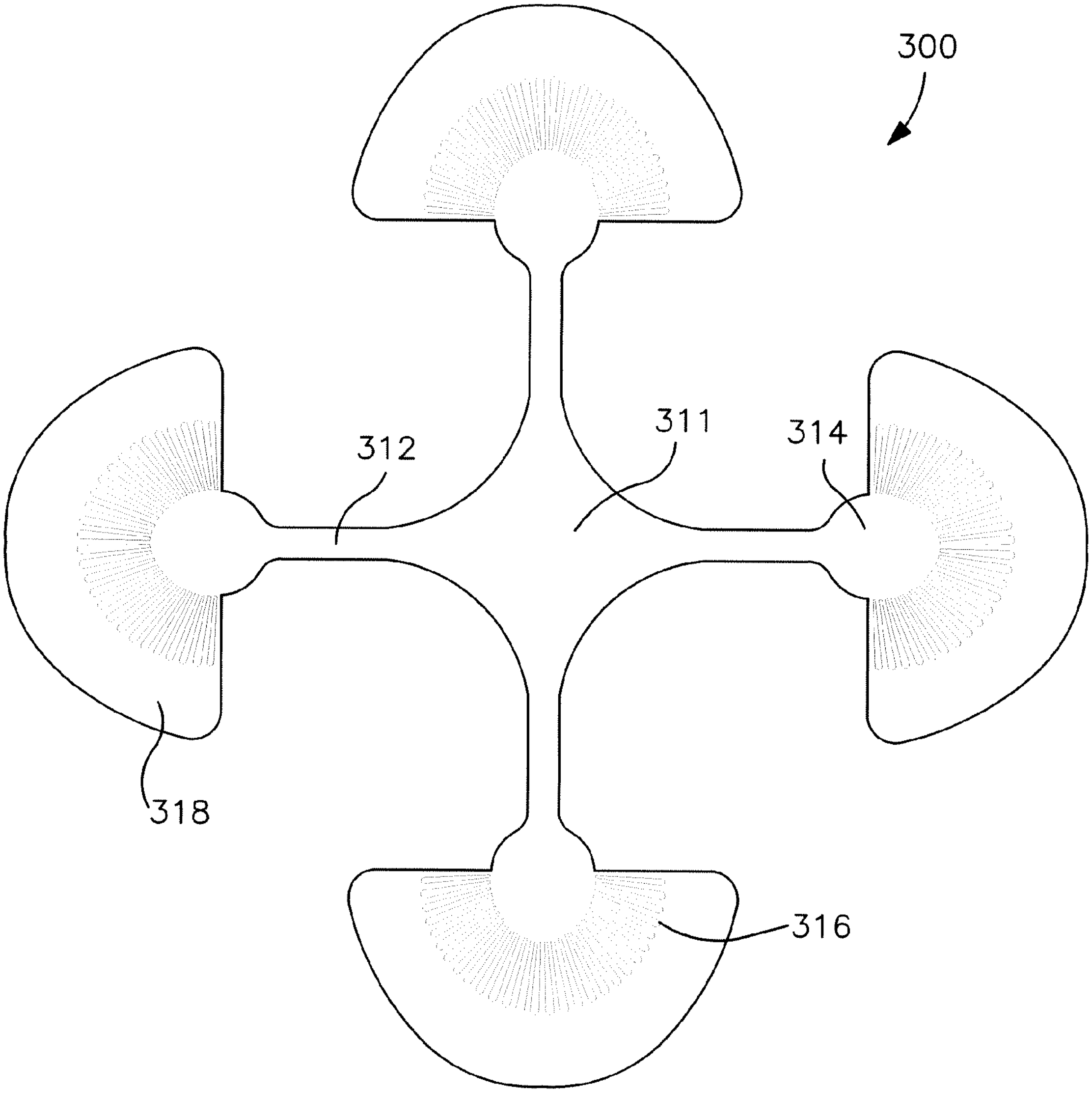

It should be understood that the embodiments discussed are merely exemplary, and that the microfluidic device of the present invention is in no way limited to the particular configuration depicted and described above. In this regard, reference is made to FIGS. 2-7, which illustrate several other embodiments of the microfluidic device of the present invention. FIGS. 2-4, for example, depict microfluidic devices 100 containing a channel 112, an analysis zone 114, a plurality of wicking channels 116, and an overflow zone 118. The analysis zone 114 in these embodiments has a circular shape in which the cross-sectional dimension of the zone 114 is simply defined by the diameter of the circle. Furthermore, FIGS. 5-6 illustrate microfluidic devices 200 containing a channel 212, an analysis zone 214, a plurality of wicking channels 216, and an overflow zone 218. Contrary to previous embodiments, the overflow zones 218 taper outwardly. Finally, FIG. 7 illustrates a microfluidic device 300 that contains a well 311 that supplies multiple channels 312. Each channel 312 is in fluid communication with an analysis zone 314, a plurality of wicking channels 316, and an overflow zone 318. The embodiment shown in FIG. 7 may be particularly useful for determining the presence or concentration of multiple analytes within a fluid test sample. A variety of other configurations will be apparent to one of skill upon full consideration of the foregoing description.

Referring again to FIG. 1, regardless of the type of fluidic zones utilized, the microfluidic device 10 typically employs a solid substrate (not shown) on or within which the fluidic zones 12, 14, 16, and 18 are disposed. The materials used to form the substrate may be selected for their compatibility with the full range of conditions to which the microfluidic devices are exposed, including extremes of pH, temperature, salt concentration, and application of electric fields. Such materials are well known to those skilled in the art. For example, the substrate may be formed of any one of a number of suitable plastics, glass, functionalized plastics and glass, silicon wafers, foils, glass, etc. Rather than a rigid substrate, thermoplastic films may also be suitable. Such films include, but are not limited to, polymers such as: polyethylene-terephthalate (MYLAR®), acrylonitrile-butadiene-styrene, acrylonitrile-methyl acrylate copolymer, cellophane, cellulosic polymers such as ethyl cellulose, cellulose acetate, cellulose acetate butyrate, cellulose propionate, cellulose triacetate, cellulose triacetate, polyethylene, polyethylene-vinyl acetate copolymers, ionomers (ethylene polymers) polyethylene-nylon copolymers, polypropylene, methyl pentene polymers, polyvinyl fluoride, and aromatic polysulfones.

Fluidic zones may be fabricated on and/or within such a solid substrate using a variety of different known techniques. For instance, some suitable microfabrication techniques include photolithography, wet chemical etching, laser ablation, air abrasion techniques, injection molding, embossing, printing, etc. In one particular embodiment, printing techniques may be utilized to form one or more microfluidic zones. Several suitable printing techniques are described in U.S. Pat. No. 5,512,131 to Kumar, et al.; U.S. Pat. No. 5,922,550 to Everhart, et al.; U.S. Pat. No. 6,294,392 to Kuhr, et al.; U.S. Pat. No. 6,509,085 to Kennedy; and U.S. Pat. No. 6,573,040 to Everhart, et al., which are incorporated herein in their entirety by reference thereto for all purposes. For example, in one embodiment, "stamp printing" is utilized to form microfluidic zones on a substrate. Some suitable stamp printing techniques are described in U.S. Pat. No. 5,512,131 to Kumar, et al. and U.S. Pat. No. 5,922,550 to Everhart, et al. For example, an elastomeric stamp may be used to transfer an ink to the substrate surface through contact. The stamp is fabricated by casting polydimethylsiloxane (PDMS) on a master having the inverse of the desired print pattern, which will thereby result in the desired channel pattern. Masters are prepared using standard photolithographic techniques, or constructed from existing materials having microscale surface features. In one embodiment, a photolithographically-produced master is placed in a glass or plastic Petri dish, and a mixture of SYLGARD® silicone elastomer 184 and SYLGARD® silicone elastomer 184 curing agent (Dow Corning Corporation) is poured over it. The polydimethylsiloxane (PDMS) elastomer is allowed to sit at room temperature and is then cured; alternately, for faster curing, the elastomer may be cured at a temperature of from about 60 to about 65° C. When cured, PDMS is sufficiently elastomeric to allow good conformal contact of the stamp and the surface of the substrate 40.

The resulting elastomeric stamp is "inked" by exposing the stamp to a solution of the desired material used to help form the fluidic channel. This is typically done by placing the stamp face down in the solution for about 10 seconds to about 10 minutes. The stamp is allowed to dry, either under ambient conditions or by exposure to a stream of air or nitrogen gas. Following inking, the stamp is applied to the surface of the substrate. Light pressure is used to ensure complete contact between the stamp and the substrate. After about 1 second to about 5 minutes, the stamp is then gently peeled from the substrate. Following removal of the stamp, the substrate may be rinsed and dried.

Stamp printing, such as described above, may be used to prepare microfluidic zones in various ways. In one embodiment, for example, the elastomeric stamp is inked with a material that significantly alters the surface energy of the substrate so that it may be selectively "wettable" to the monomer or pre-polymer (if post-cured), or polymer used to make the zone. The stamp could have raised features to print the desired channel pattern. An exemplary stamp printing method may involve inking the stamp with a wetting agent, such as hydrophilic self-assembling monolayers (SAMs), including those that are carboxy-terminated. Various examples of such self-assembling monolayers are described in U.S. Pat. No. 5,922,550 to Everhart, et al. In another embodiment, hydrophobic wetting agents may be utilized. Specifically, the inverse of the desired pattern is stamp printed onto a hydrophilic substrate. Upon exposure of the monomer or pre-polymer (if post-cured), or polymer, the inks would selectively wet only on the substrate, thereby resulting in the desired channel pattern.

Another stamp printing technique might simply involve inking an elastomeric stamp with a solution of the monomer or pre-polymer (if post-cured), or polymer. The stamp may have raised features to match the desired channel pattern so that a direct transfer of the channel-forming material would occur on the substrate. Still another suitable contact printing technique that may be utilized is "screen printing." Screen printing is performed manually or photomechanically. The screens may include a silk or nylon fabric mesh with, for instance, from about 40 to about 120 openings per lineal centimeter. The screen material is attached to a frame and stretched to provide a smooth surface. The stencil is applied to the bottom side of the screen, i.e., the side in contact with the substrate upon which the fluidic zones are to be printed. The print material is painted onto the screen, and transferred by rubbing the screen (which is in contact with the substrate) with a squeegee.

In addition to contact printing, any of a variety of well-known non-contact printing techniques may also be employed in the present invention. In one embodiment, for example, ink-jet printing may be employed. Ink-jet printing is a non-contact printing technique that involves forcing ink through a tiny nozzle (or a series of nozzles) to form droplets that are directed toward the substrate. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the fluidic channels are formed from a dielectric material, DOD printing techniques may be more desirable.

In addition to the printing techniques mentioned above, any other suitable printing technique may be used in the present invention. For example, other suitable printing techniques may include, but not limited to, such as laser printing, thermal ribbon printing, piston printing, spray printing, flexographic printing, gravure printing, etc. Further, various other non-printing techniques may also be used in the present invention. For instance, some examples of other techniques that may be used in the present invention to form the microfluidic device are described in U.S. Pat. No. 6,416,642 to Alajoki, et al., which is incorporated herein in its entirety by reference thereto for all purposes.

B. Detection Techniques

Generally speaking, any type of assay may be utilized in the present invention, including homogeneous and heterogeneous immunoassays. A homogeneous assay is an assay in which uncomplexed labeled species are not separated from complexed labeled species. A heterogeneous assay is an assay in which uncomplexed labeled species are separated from complexed labeled species. Separation may be carried out by physical separation, e.g., by transferring one of the species to another reaction vessel, filtration, centrifugation, chromatography, solid phase capture, magnetic separation, and so forth, and may include one or more washing steps. The separation may also be nonphysical in that no transfer of one or both of the species is conducted, but the species are separated from one another in situ. In one particular embodiment, for example, a heterogeneous immunoassay is utilized. Such immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that may be used to determine the presence or concentration of that particular antigen in a fluid test sample.

Any of a wide variety of detection techniques may also be utilized in the present invention. In one particular embodiment, for example, diffraction-based detection techniques may be utilized. The term "diffraction" refers to the phenomenon observed when waves are obstructed by obstacles caused by the disturbance spreading beyond the limits of the geometrical shadow of the object. The effect is marked when the size of the object is of the same order as the wavelength of the waves. For diffraction-based detection techniques, the obstacles are analytes (with or without attached particles) and the waves are light waves. For example, various examples of diffraction-based assay devices are described in U.S. Pat. No. 6,221,579 to Everhart, et al., which is incorporated herein in its entirety by reference thereto for all purposes. For purposes of illustration only, one embodiment of a diffraction-based detection technique that may be employed in the present invention will now be described in more detail.

For example, a separation medium, such as a porous membrane, polymer film, etc., may be utilized to perform the assay. To facilitate diffraction-based detection, the separation medium may optionally be applied with a metal coating. Such a separation medium with a metal coating thereon may have an optical transparency of from about 5% to about 95%, and in some embodiments, from about 20% to about 80%. In one embodiment, the separation medium has at least about 80% optical transparency, and the thickness of the metal coating is such as to maintain an optical transparency greater than about 20%, so that diffraction patterns may be produced by either reflected or transmitted light. This corresponds to a metal coating thickness of about 10 to about 20 nanometers. However, in other embodiments, the metal thickness may be between approximately 1 nanometer and 1000 nanometers. The preferred metal for deposition on the film is gold. However, silver, aluminum, chromium, copper, iron, zirconium, platinum, titanium, and nickel, as well as oxides of these metals, may be used. Chromium oxide may be used to make metallized layers. Besides a metal coating, a surface of the separation medium may also be treated with other materials, e.g., derivatized or coated surfaces, to enhance their utility in the microfluidic system, e.g., provide enhanced fluid direction. In addition, an insulating layer, e.g., silicon oxide, may be formed on the separation medium, particularly in those applications in which electric fields are applied to the device or its contents.

A receptive material may also be applied to the separation medium that is capable of binding to the analyte of interest or a complex thereof. The receptive material may be a biological receptive material. Such biological receptive materials are well known in the art and may include, but are not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof. Any suitable method may be utilized to apply the receptive material. The receptive material may be applied so that it partially or uniformly covers the surface (for example, upper) of the separation medium. Although not required, non-contact methods for applying the receptive material may be desired so as to eliminate the possibility of contamination by contact during application. Suitable application methods include, but are not limited to, dipping, spraying, rolling, spin coating, and any other technique wherein the receptive material layer may be applied generally uniformly over the entire test surface of the separation medium. Simple physisorption may occur on many materials, such as polystyrene, glass, nylon, or other materials well known to those skilled in the art. One particular embodiment of immobilizing the receptive material layer involves molecular attachment, such as that possible between thiol or disulfide-containing compounds and gold. For example, a gold coating of about 5 to about 2000 nanometers thick may be supported on a silicon wafer, glass, or polymer film (e.g., MYLAR® film). The receptive material attaches to the gold surface upon exposure to a solution thereof. The receptive material layer may also be formed on a separation medium as a self-assembling monolayer of alkanethiolates, carboxylic acids, hydroxamic acids, and phosphonic acids on metallized thermoplastic films. The self-assembling monolayer has the receptive material bound thereto. For instance, U.S. Pat. No. 5,922,550, which is incorporated herein in its entirety by reference thereto for all purposes, provides a more detailed description of such self-assembling monolayers and methods for producing the monolayers.

Once the receptive material layer is applied to the separation medium, a mask (not shown) is then placed over the medium, and the mask is irradiated with an energy source. In its basic form, the "mask" serves to shield or "protect" at least one area or section of the receptive material from the irradiating energy source and to expose at least one adjacent section to the energy source. For example, the mask may be a generally transparent or translucent blank (e.g., a strip of material) having any pattern of shielded regions printed or otherwise defined thereon. The exposed unshielded regions of the mask correspond to the exposed areas of the separation medium. Alternatively, the mask may simply be a single object placed upon the separation medium. The area under the object would be protected and thus define an active area of the receptive material, and the area around the object would be exposed to the energy source and thus define an area of inactive receptive material. Alternatively, the object may have any pattern of openings defined therethrough corresponding to the exposed areas.

The mask may be formed of any suitable material that protects the underlying portion of the separation medium from the irradiating energy source. A material that has proven useful for defining patterns of active and inactive receptive material regions on a gold-plated MYLAR® film coated with an antibody solution is a transparent or translucent polymer film (such as MYLAR®) having a pattern of shielded or protected regions printed thereon. This type of mask is useful for light sources with a wavelength equal or greater than about 330 nanometers. For light sources having a wavelength below about 330 nanometers, a quartz or fused silica mask having chrome or other metal-plated shielded regions defined thereon may be used. It may be desired to select a hole pattern and size so as to maximize the visible diffraction contrast between the active and inactive regions. As one example of a pattern, it has been found suitable if the active regions are defined as generally circular with a diameter of about 10 microns and spaced from each other by about 5 microns. However, other patterns that provide a defined diffraction image would be suitable.

The energy source is selected so that the receptive material exposed by the mask is rendered inactive or incapable of binding analyte. Without being limited by theory, one likely mechanism is that the energy source essentially destroys the bond structure of the receptive material by a radical mechanism. The energy source is selected so that the receptive material exposed by the mask is rendered inactive. The energy source essentially destroys the bond structure of the receptive material by a radical mechanism. The receptive material under the shielded areas of the mask is protected during the irradiation step. Thus, upon removal of the mask, a pattern of active and inactive receptive material areas are defined. It should be understood that the term "pattern" includes as few as one active area and one inactive area. Upon subsequent exposure of the diffraction-based assay device to a medium containing the analyte of interest, such analyte will bind to the receptive material in the active areas. The analyte results in diffraction of transmitted and/or reflected light in a visible diffraction pattern corresponding to the active areas.

Any suitable energy source may be selected for irradiating the mask and separation medium combination. The energy source may be, for example, a light source, e.g., an ultraviolet (UV) light source, an electron beam, a radiation source, etc. In one particular embodiment, the receptive material is a protein-based material, such as an antibody, and the deactivating energy source is a UV light source. The sensor would be exposed to the UV source for a period of time sufficient for deactivating the antibody. Wavelengths and exposure times may vary depending on the particular type of receptive material. Other suitable energy sources may include tuned lasers, electron beams, various types of radiation beams including gamma and X-ray sources, various intensities and wavelengths of light including light beams of sufficient magnitude at the microwave and below wavelengths, etc. It should be appreciated that any number of energy sources may be specifically tailored for deactivating a particular antibody or other type of biomolecule. Care should be taken that the energy source does not damage (e.g., melt) the underlying separation medium or mask.

In some cases, such as when the analyte is too small to be easily detected, detection probes may be employed for labeling the analyte. Any substance generally capable of generating a signal that is detectable visually or by an instrumental device may be used. Various suitable detectable substances may include chromogens; luminescent compounds (e.g., fluorescent, phosphorescent, etc.); radioactive compounds; visual labels (e.g., latex particles or colloidal metallic particles, such as gold); liposomes or other vesicles containing signal producing substances; and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes.

The detectable substances may be used alone or in conjunction with a microparticle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), oxide particles (e.g., silica, titanium diode, etc.), and so forth, may be used. Further, synthetic particles may also be utilized. For example, in one embodiment, latex particles that are labeled with a fluorescent or colored dye are utilized. Although any latex particle may be used in the present invention, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable microparticles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 1000 nanometers, in some embodiments from about 10 to about 600 nanometers, and in some embodiments, from about 20 to about 400 nanometers.

In some instances, it may also be desired to modify the detection probes in some manner so that they are more readily able to bind to the analyte. In such instances, the detection probes may be modified with certain specific binding members that are adhered thereto to form conjugated probes. Specific binding members generally refer to a member of a specific binding pair, i.e., two different molecules where one of the molecules chemically and/or physically binds to the second molecule. For instance, immunoreactive specific binding members may include antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding pairs include but are not limited to, biotin and avidin (or derivatives thereof), biotin and streptavidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and so forth. Furthermore, specific binding pairs may include members that are analogs of the original specific binding member. For example, a derivative or fragment of the analyte, i.e., an analyte-analog, may be used so long as it has at least one epitope in common with the analyte.

The specific binding members may generally be attached to the detection probes using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer because the surface of the detection probe may contain a relatively high surface concentration of polar groups. In addition, although detection probes are often functionalized after synthesis, in certain cases, such as poly(thiophenol), the probes are capable of direct covalent linking with a protein without the need for further modification. Besides covalent bonding, other attachment techniques, such as physical adsorption, may also be utilized.

To form a microfluidic assay device in accordance with the present invention, the separation medium may be placed adjacent to the substrate having one or more fluidic zones. Although not required, the separation medium and substrate are generally laminated together to form a liquid-tight seal. For instance, suitable bonding techniques may include adhesive bonding, ultrasonic bonding, thermal diffusion bonding, etc. During use, a fluid test sample is applied to a sample well and/or to the input channel. The fluid test sample may contain the analyte of interest and optionally reagents for performing the assay (e.g., detection probes). Thus, apart from serving as a location for applying the fluid test sample, the sample addition well and/or the input channel may also serve as a location for mixing, diluting, or reacting reagents used in the device. Alternatively, the assay reagents may be applied to the separation medium (e.g., via dehydration) where they may become re-suspended in the fluid test sample upon contact therewith. For example, the separation medium may be laminated to the substrate so that the dehydrated assay reagents are positioned adjacent to the input channel. In still other embodiments, the desired assay reagents may simply be applied to the analysis zone. Regardless, the fluid test sample flows through the device until it reaches the analysis zone. The separation medium is generally positioned close enough to the analysis zone so that an analyte or complex thereof contained within the fluid is capable of binding to the receptive material for detection.

In the embodiments described above, separate components are utilized to form the microfluidic assay device. That is, the assay device employs a substrate formed with fluidic zones and a separation medium applied with a receptive material. The combination of the substrate and separation medium forms a microfluidic device that is capable of detecting the presence or quantity of an analyte. It should be understood, however, that the present invention also encompasses embodiments in which only a single component is utilized. For example, a receptive material may be applied directly to the surface of the fluidic zone-containing substrate using any of the techniques described above. In one embodiment, the receptive material is applied directly to a metal coating present on the substrate within the analysis zone. In this manner, a fluid test sample may flow through the input channel and into the analysis zone where the analyte (or complex thereof) may bind to the receptive material.

In addition, any known type of assay or detection technique may be utilized in the present invention. For example, other known optical detection techniques may be utilized, such as phosphorescence, fluorescence, absorbance, etc. As an example, an optical detector may employ a light source and detector, which are optionally positioned adjacent to an optical detection window formed over the analysis zone. Further, the microfluidic device may also employ electrochemical detection techniques, which typically involve the detection of an electrochemical reaction between an analyte (or complex thereof) and a capture ligand on an electrode strip. Various exemplary electrochemical detection systems are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

Regardless of the specific detection mechanism utilized, the microfluidic device of the present invention allows for the performance of an assay in a "single step" without the need for active forces, such as a pressure source, electrokinetic force, etc., to induce flow of the fluid test sample through the device. Likewise, flow rate is controlled so that the total dwell time of the fluid test sample within the analysis zone is long enough to allow for completion of the desired reactions and/or detection.

The present invention may be better understood with reference to the following examples.

Example 1

The ability to form a microfluidic device in accordance with one embodiment of the present invention was demonstrated. Specifically, a micromolded polymer sheet was initially formed from polydimethylsiloxane (PDMS) silicone rubber ("Sylgard 184", available from Dow Corning of Midland, Mich.). The PDMS prepolymer was a liquid having a viscosity of 3900 centipoise. The PDMS prepolymer was polymerized with a radical-mediated mechanism that employed a platinum-based catalyst (1 part catalyst: 10 parts prepolymer). The initial liquid properties of the PDMS allowed it to replicate finely structured molds with high fidelity and good dimensional stability.

A 50-micrometer thick photoresist (available from Dow Chemical under the name "EPON SU-8") was then formed on a silicon wafer. Specifically, 3 milliliters of the SU-8 photoresist was dispensed at 100 RPM onto a 6" diameter silicon wafer, ramped slowly to 500 RPM, and then ramped quickly to 2000 RPM and held for 30 seconds. The deposited photoresist was soft-baked on a contact hot plate (65° C. for 2 minutes and then 95° C. for 5 minutes). Using an LS-1000 Solar Simulator (Solar Light of Philadelphia, Pa.), the SU-8 photoresist was then exposed for 30 seconds with a chrome-patterned quartz photomask having a pre-designed fluidic zone pattern. The design for the fluidic zones was created using a CAD program. The design is shown in FIG. 1 and had the following dimensions.

TABLE 1

| | Dimensions of the Fluidic Zones | | | |
|---|---|---|---|---|
| | Volume (nanoliters) | Width (micrometers) | Depth (micrometers) | Aspect Ratio |
| Input channel | 86 | 400 | 50 | 8 |
| Analysis Zone | 246 | 2500 (max) | 50 | 50 |
| Wicking Channels (92×) | 2370 | 50 | 50 | 1 |
| Overflow Zone | 1108 | 1100 | 50 | 22 |
| TOTAL | 3810 | | | |

Following a 7-minute post exposure bake at 95° C. on a contact hot plate, a master mold was developed through immersion in an SU-8 developer (MicroChem of Newton, Mass.) for about 6 minutes, followed by a spin dry cycle (2000 RPM, 30 seconds). Finally, the pattern was cleansed via a dynamic isopropanol rinse cycle (1 mL) using the aforementioned spin dry conditions. The resulting negative relief master was used to cast a positive PDMS microfluidic device. Once cured, the PDMS micromolded fluidic was carefully removed from the mold and then adhered to a film. The surface energy of the PDMS part was such that it formed a liquid-tight bond when placed into intimate contact with the film.

The film was obtained from CPFilms, Inc. of Martinsville, Va., and was a 7-mil Mylar® film having a 10-nanometer thick gold coating (≦13 ohms per square inch). The gold-coated film was exposed to a thiolated, monoclonal antibody reactive toward CRP (BiosPacific) for 2 minutes. The film was then rinsed with distilled, deionized water and blown dry with 0.2-micron filtered air. The coated film was mounted on a vacuum platen and the chrome-patterned quartz photomask was placed directly in contact with the coated side of the film. The space between the mask and film was reduced even further by pulling a strong vacuum. The coated film was then exposed to 222-nanometer light (monochromatic, generated by a pair of KrF excimer lamp bulbs obtained from Heraeus Noblelight of Duluth, Ga.) for 2 minutes. The mobile phase of the assay device was formed from 300-nanometer diameter carboxylate-modified, latex microspheres (Bangs Laboratories). Monoclonal anti-CRP antibody (BiosPacific) was conjugated to the latex microspheres and the particles were stored at a concentration of 1.25% solids in phosphate buffered saline (PBS) and Triton X-100 (0.3%) at a pH of 7.2.

Figure 8:
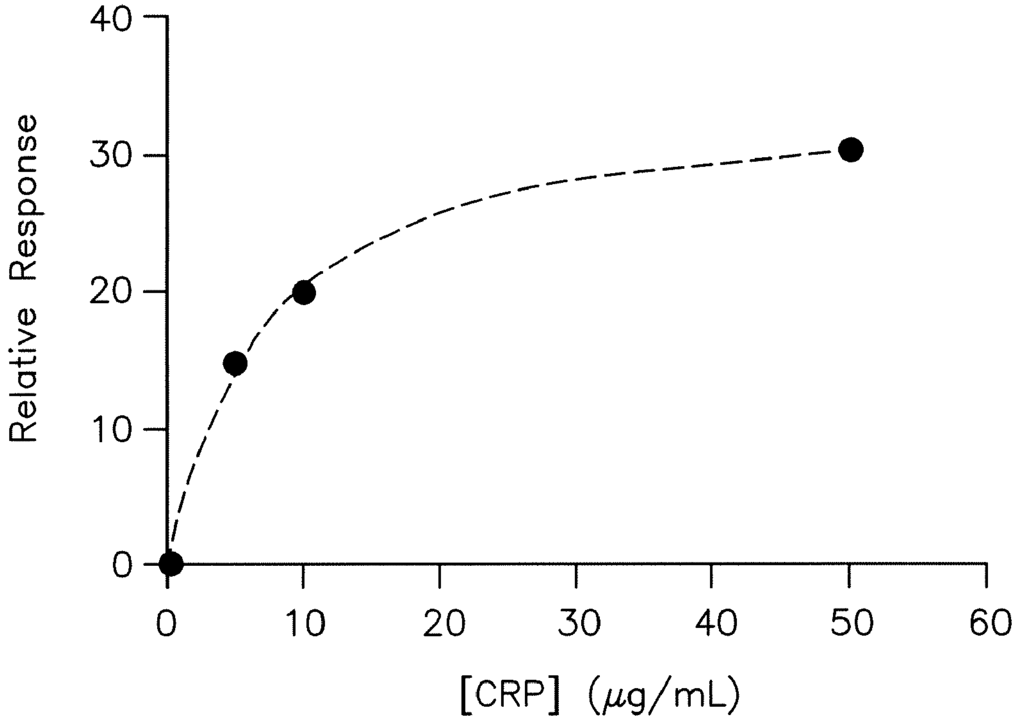
FIG. 8 is the dose response curve obtained in Example 1, in which the relative response is plotted versus the concentration of C-reactive protein (micrograms per milliliter).

To initiate the assay, the conjugated particles were premixed with samples that contained varying concentrations of C-reactive protein, and the resulting mixtures were applied to the input channel of the assembled microfluidic device. The mixtures flowed into the input channel, filled the analysis zone, and eventually began to flow into the wicking channels. After 3 to 5 minutes, the wicking channels filled to such a degree that the input channel and eventually the analysis zone were cleared of liquid. The receding air/liquid interface carried away any unbound mobile phase, leaving only signal particles in the analysis zone where there was enough analyte to form a "sandwich" structure. Results were obtained using a diffraction-based detection technique, such as described in 2003/0107740 to Kaylor, et al., which is incorporated herein in its entirety by reference thereto for all purposes. The experiment was repeated at varying analyte concentrations to generate the dose-response curve shown in FIG. 8.

Example 2

A microfluidic device was formed as described in Example 1, except that the design utilized is shown in FIG. 2 and had the following dimensions.

TABLE 2

| | Dimensions of the Fluidic Zones | | | |
|---|---|---|---|---|
| | Volume (nanoliters) | Width (micrometers) | Depth (micrometers) | Aspect Ratio |
| Input Channel | 165 | 400 | 50 | 8 |
| Analysis Zone | 260 | 3000 (max) | 50 | 60 |
| Wicking Channels (20×) | 450 | 50 | 50 | 1 |
| Overflow Zone | 9240 | 2200 | 50 | 44 |
| TOTAL | 10,115 | | | |

Example 3

A microfluidic device was formed as described in Example 1, except that the design utilized is shown in FIG. 3 and had the following dimensions.

TABLE 3

| | Dimensions of the Fluidic Zones | | | |
|---|---|---|---|---|
| | Volume (nanoliters) | Width (micrometers) | Depth (micrometers) | Aspect Ratio |
| Input Channel | 165 | 400 | 50 | 8 |
| Analysis Zone | 240 | 2000 (max) | 50 | 50 |
| Wicking Channels (20×) | 450 | 50 | 50 | 1 |
| Overflow Zone | 9240 | 2200 | 50 | 44 |
| TOTAL | 10,095 | | | |

Example 4

A microfluidic device was formed as described in Example 1, except that the design utilized is shown in FIG. 4 and had the following dimensions.

TABLE 4

| | Dimensions of the Fluidic Zones | | | |
|---|---|---|---|---|
| | Volume (nanoliters) | Width (micrometers) | Depth (micrometers) | Aspect Ratio |
| Input Channel | 89 | 200 | 50 | 4 |
| Analysis Zone | 160 | 2000 (max) | 50 | 40 |
| Wicking Channels (50×) | 927 | 100 | 50 | 2 |
| Overflow Zone | 1987 | 2000 | 50 | 40 |
| TOTAL | 3163 | | | |

Example 5

A microfluidic device was formed as described in Example 1, except that the design utilized is shown in FIG. 5 and had the following dimensions.

TABLE 5

| | Dimensions of the Fluidic Zones | | | |
|---|---|---|---|---|
| | Volume (nanoliters) | Width (micrometers) | Depth (micrometers) | Aspect Ratio |
| Input Channel | 219 | 200 | 50 | 5 |
| Analysis Zone | 163 | 2000 (max) | 50 | 40 |
| Wicking Channels (55×) | 3440 | 50 to 200 (tapered) | 50 | 2 to 4 (tapered) |
| Overflow Zone | 14,129 | 5000 | 50 | 100 |
| TOTAL | 17,951 | | | |

Example 6

A microfluidic device was formed as described in Example 1, except that the design utilized is shown in FIG. 6 and had the following dimensions.

TABLE 6

| | Dimensions of the Fluidic Zones | | | |
|---|---|---|---|---|
| | Volume (nanoliters) | Width (micrometers) | Depth (micrometers) | Aspect Ratio |
| Input Channel | 218 | 250 | 50 | 5 |
| Analysis Zone | 158 | 2000 (max) | 50 | 40 |
| Wicking Channels (55×) | 1195 | 50 | 50 | 1 |
| Overflow Zone | 14,123 | 5000 | 50 | 100 |
| TOTAL | 15,694 | | | |

Example 7

A microfluidic device was formed as described in Example 1, except that the design utilized is shown in FIG. 7 and had the following dimensions.

TABLE 7

| | Dimensions of the Fluidic Zones | | | |
|---|---|---|---|---|
| | Volume (nanoliters) | Width (micrometers) | Depth (micro-meters) | Aspect Ratio |
| Central Zone | 1254 | 3500 | 50 | 70 |
| Input Channel (4×) | 106 | 1000 | 50 | 20 |
| Analysis Zone (4×) | 1552 | 3000 (max) | 50 | 60 |
| Wicking Channels (120×) | 6526 | 100 to 350 (tapered) | 50 | 2 to 7 (tapered) |
| Overflow Zone (4×) | 3456 | 1100 | 50 | 22 |
| TOTAL | 12,894 | | | |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An assay device for detecting the presence or concentration of an analyte within a fluid test sample, said assay comprising:

an input channel;

an analysis zone in fluid communication with said input channel, said analysis zone defining a periphery, wherein said analysis zone serves as a location for detecting the analyte;

from 3 to about 500 microfluidic wicking channels extending radially from the periphery of said analysis zone, wherein the assay device is configured so that the fluid test sample is capable of flowing through said input channel and said analysis zone primarily via capillary action, and an absorbent material positioned within all of the wicking channels.

2. The assay device of claim 1, wherein said input channel has a cross-sectional area of less than about 20 square millimeters.

3. The assay device of claim 1, wherein said analysis zone is of a size sufficient to accommodate substantially the entire volume of the fluid test sample applied to the assay device.

4. The assay device of claim 1, wherein said analysis zone has a substantially circular shape.

5. The assay device of claim 1, wherein the fluid test sample is capable of flowing sequentially from said input channel to said analysis zone.

6. The assay device of claim 1, wherein said wicking channels taper inwardly toward said analysis zone.

7. The assay device of claim 1, wherein said wicking channels have an aspect ratio of from about 0.1 to about 10.

8. The assay device of claim 1, wherein said wicking channels have an aspect ratio of from about 0.25 to about 5.

9. The assay device of claim 1, wherein said wicking channels have an aspect ratio of from about 0.5 to about 1.5.

10. The assay device of claim 1, wherein said wicking channels have a cross-sectional area of less than about 20 square millimeters.

11. The assay device of claim 1, wherein said wicking channels have a cross-sectional area of from about 0.001 to about 10 square millimeters.

12. The assay device of claim 1, wherein said wicking channels have a cross-sectional area of from about 0.01 to about 5 square millimeters.

13. The assay device of claim 1, wherein the assay device comprises from about 15 to about 200 of said wicking channels.

14. The assay device of claim 1, further comprising an overflow zone that is in fluid communication with said wicking channels.

15. The assay device of claim 1, further comprising a substrate on or within which said input channel, said analysis zone, and said wicking channels are disposed.

16. The assay device of claim 15, wherein a separation medium is laminated to said substrate, said separation medium containing a receptive material that is capable of binding to the analyte or a complex thereof.

17. The assay device of claim 16, wherein said separation medium includes a polymer film having a metal coating.

18. An assay device for detecting the presence or concentration of an analyte within a fluid test sample, said assay comprising:

an input channel;

a substantially circular analysis zone in fluid communication with said input channel, said analysis zone defining a periphery, wherein said analysis zone serves as a location for detecting the analyte;

from 3 to about 500 wicking channels extending radially from the periphery of said analysis zone, wherein said wicking channels have an aspect ratio of from about 0.1 to about 10 and a cross-sectional area of less than about 20 square millimeters;

an absorbent material positioned within one or more of the wicking channels; and an overflow zone that is in fluid communication with and directly connected to each of the wicking channels, wherein the assay device is configured so that the fluid test sample is capable of flowing through said input channel and said analysis zone primarily via capillary action.

19. The assay device of claim 1, wherein said wicking channels are spaced about equidistant from each other.

20. The assay device of claim 1, wherein the assay device comprises from about 20 to about 80 of said wicking channels.

21. The assay device of claim 1, wherein the assay device is configured so that the fluid test sample is capable of flowing through said input channel and said analysis zone without the use active forces to induce fluid flow of the fluid test sample.

22. The assay device of claim 18, wherein the overflow zone is interconnected such that each wicking channel is directly connected to the same overflow zone.

23. The assay device of claim 1, wherein the absorbent material comprises nitrocellulose.

24. The assay device of claim 1, wherein the absorbent material comprises cellulosic materials.

25. The assay device of claim 1, wherein the absorbent material comprises glass fiber filter paper.

* * * * *